US00PP16186P2

(12) United States Plant Patent
Zary

(10) Patent No.: US PP16,186 P2
(45) Date of Patent: Jan. 3, 2006

(54) HYBRID TEA ROSE PLANT NAMED 'JACDOUCE'

(50) Latin Name: *Rosa hybrida*
Varietal Denomination: JACdouce

(75) Inventor: Keith W. Zary, Somis, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/849,353

(22) Filed: May 18, 2004

(51) Int. Cl.
*A01H 5/00* (2006.01)

(52) U.S. Cl. ..... Plt./135
(58) Field of Classification Search ..... Plt./135, Plt./136
See application file for complete search history.

*Primary Examiner*—Anne Marie Grunberg
*Assistant Examiner*—June Hwu
(74) *Attorney, Agent, or Firm*—Klarquist Sparkman LLP

(57) ABSTRACT

A hybrid tea rose plant having long stems bearing thick petaled, orange flowers having long vase life, the plant having an upright angular growth, and the ability to grow its own roots.

1 Drawing Sheet

Genus and species: *Rosa hybrida.*
Variety denomination: 'JACdouce'.

ORIGIN OF THE INVENTION

The present invention relates to a new and distinct variety of a hybrid tea rose plant named 'JACdouce' which was originated by me by crossing an unnamed seedling (not patented) with the variety 'DICjana' (Elina) (not patented).

BACKGROUND OF THE INVENTION

The primary objective of this breeding was to produce a new rose variety having the bright flower color of the male parent combined with the higher petal count, vigorous plant and health of the female parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Bright orange flower color;
2. Thick petals;
3. Long vase life;
4. Upright angular growth;
5. Long cutting stems; and
6. Ability to grow on its own roots.

Asexual reproduction of this new variety by rooting cuttings, as performed at Wasco, Calif., shows that the foregoing and all other characteristics and distinctions come true to form and are established and transmitted through succeeding propagations.

Comparison with Parents

'JACdouce' differs from its male parent, 'DICjana', in having ten more petals, longer cutting stems and a more angular growth habit. It differs from its female parent in having an orange flower as compared to the light yellow flower of the female parent and in having longer stems, therefore being taller than its parent.

Comparison with Similar Variety

'JACdouce' differs from 'JACirst' (Artistry) (U.S. Plant Pat. No. 10,230) in flower color being more of a bright orange than 'JACirst', and in having a longer vase life, 11–12 days versus 8–9 for 'JACirst'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed seedling (Unnamed seedling× Unnamed seedling).
*Pollen parent.*—'DICjana' (Elina) (not patented).

FLOWER

Observations made from January 2002 to October 2003 of plants commencing at two years of age grown in a garden environment at Somis, Calif.

Blooming habit: Continuous.

Bud:
*Size.*—About 4 cm. long and 2 cm. in diameter when the petals start to unfurl.
*Form.*—The bud form is long and pointed ovoid.
*Color.*—When sepals first divide, bud color is Orange-Red Group N30B. When half blown, the upper sides of the petals are Orange-Red Group N30C; and the lower sides of the petals are Orange-Red Group 30C.

*Sepals.*—Color: Upper Surface: Green Group 138C with overlay of Greyed-White Group 156D. Lower surface: Yellow-Green Group 144B occasionally streaked with Greyed-Red Group 181A. Length: 36–42 mm. Width: 11–13 mm. Shape: Subulate. Surface texture: Upper surface: Canescent. Lower surface: Glandular. There are three normally appendaged sepals. There are two unappendaged sepals with ciliolate edges.

*Receptacle.*—Color: Green Group 143C. Shape: Funnel. Size: Small, about 5 mm. long×9 mm. wide. Surface: Smooth.

*Peduncle.*—Length: Long, averaging about 10 cm. Surface: Glandular. Color: Green Group 143C, often appears Greyed-Red Group 178A in bright sunlight. Strength: Stiff and erect.

Bloom:

*Size.*—Medium. Average open diameter is about 9 cm.

*Borne.*—Singly.

*Stems.*—Strength: Strong. Average length is about 30–40 cm. with a diameter of 5–7 mm.

*Form.*—When first open: High, centered. Permanence: All petals curl quill fashion.

*Petalage.*—Number of petals under normal conditions: 35–40.

*Color.*—The upper sides of the petals are Orange-Red Group N30C. The reverse sides of the petals are Orange-Red Group 30C. The base of each petal is Yellow Group 9B. The major color on the upper side is Orange-Red N30C.

*Variegations.*—None.

*Discoloration.*—The general tonality at the end of the first day and through third day: Orange Red Group N30C. By the end of the fifth day color changes Red Group 41B.

*Fragrance.*—None.

Petals:

*Texture.*—Thick.

*Shape.*—Obovate.

*Size.*—Length: 40–45 mm. Width: 40–45 mm.

*Surface.*—Smooth.

*Margin.*—Entire. Apex Shape: Obtuse. Base Shape: Cuneate.

*Form.*—Moderately quilled.

*Arrangement.*—Imbricated.

*Petaloids.*—None.

*Persistence.*—Petals drop off cleanly before drying.

*Lastingness.*—On the plant: Long (about 8 days). As a cut flower: Very long (about 11–12 days).

Reproductive parts:

*Stamens.*—Number: 155–165. Length: 11–12 mm. Anthers: Length: 3 mm. Color: Yellow-Orange Group 22B. Filaments: Color: Yellow-Orange Group 22A. Length: 8–9 mm. Pollen: Color: Orange Group 26B.

*Pistils.*—Number: 50–55. Length: 6–8 mm. Styles: Color: Red Group 45C. Length: 5–7 mm. Stigmas: Color: Yellow-White Group 158B. Length: 1 mm.

*Hips.*—None observed.

PLANT

*Form.*—Bush.

*Growth.*—Vigorous, upright and angular branching.

*Age at maturity.*—2 years.

*Mature plant.*—Height: 180 cm. Width: 150 cm.

*Rootstock.*—Own roots.

Foliage: Number of leaflets on normal mid-stem leaves: 5 or 7.

*Size.*—Medium, about 13–14 cm. long×8–9 cm. wide.

*Quantity.*—Abundant.

*Color.*—New foliage: Upper side: Greyed-Red Group 178A. Lower side: Greyed-Red Group 178A. Old foliage: Upper side: Green Group 139A. Lower side: Green Group 139C.

Leaflets:

*Size.*—About 4 cm. long×3 cm. wide.

*Shape.*—Pointed oval.

*Base shape.*—Oblique.

*Apex shape.*—Acuminate.

*Texture.*—Leathery and glossy.

*Edge.*—Serrated.

*Serrations.*—Single.

*Petiole.*—Color: Yellow-Green Group 147B. Surface Texture: Smooth.

*Petiole rachis.*—Color: Yellow-Green Group 148D. Underside: Smooth with prickles.

*Stipules.*—Length: 14–16 mm (smooth and edged in many glands.). Color: Upper Surface: Yellow-Green Group 139A. Lower Surface: Yellow-Green Group 139C.

*Disease resistance.*—Susceptible to mildew and black-spot and resistant to rust under normal growing conditions.

*Pest resistance.*—None observed.

*Vein color.*—Yellow-Green Group 146B.

*Venation pattern.*—Reticulate.

Wood:

*New wood.*—Color: Greyed-Red Group 178A. Bark: Smooth.

*Old wood.*—Color: Green Group 143C. Bark: Smooth.

Prickles:

*Quantity.*—On main canes from base: 25–30 per 15 cm of stem. On laterals from main canes: 25–30 per 15 cm of stem.

*Form.*—Hooked slightly downward.

*Length.*—5 mm.

*Color when young.*—Greyed-Purple Group 184B.

*Color when mature.*—Greyed-Red Group 178B.

Small prickles:

*Quantity.*—On main stalks: 25–30 per 15 cm of stem. On laterals: 25–30 per 15 cm of stem.

*Color.*—Greyed-Green Group 191B.

*Length.*—2–3 mm.

Winter hardiness: Hardy to Zone 5.

I claim:

1. A new and distinct variety of rose plant of the hybrid tea class, substantially as herein shown and described, characterized particularly by its long stems bearing bright orange flowers having thick petals and long vase life, its upright angular growth, and the ability to grow its own roots.

* * * * *

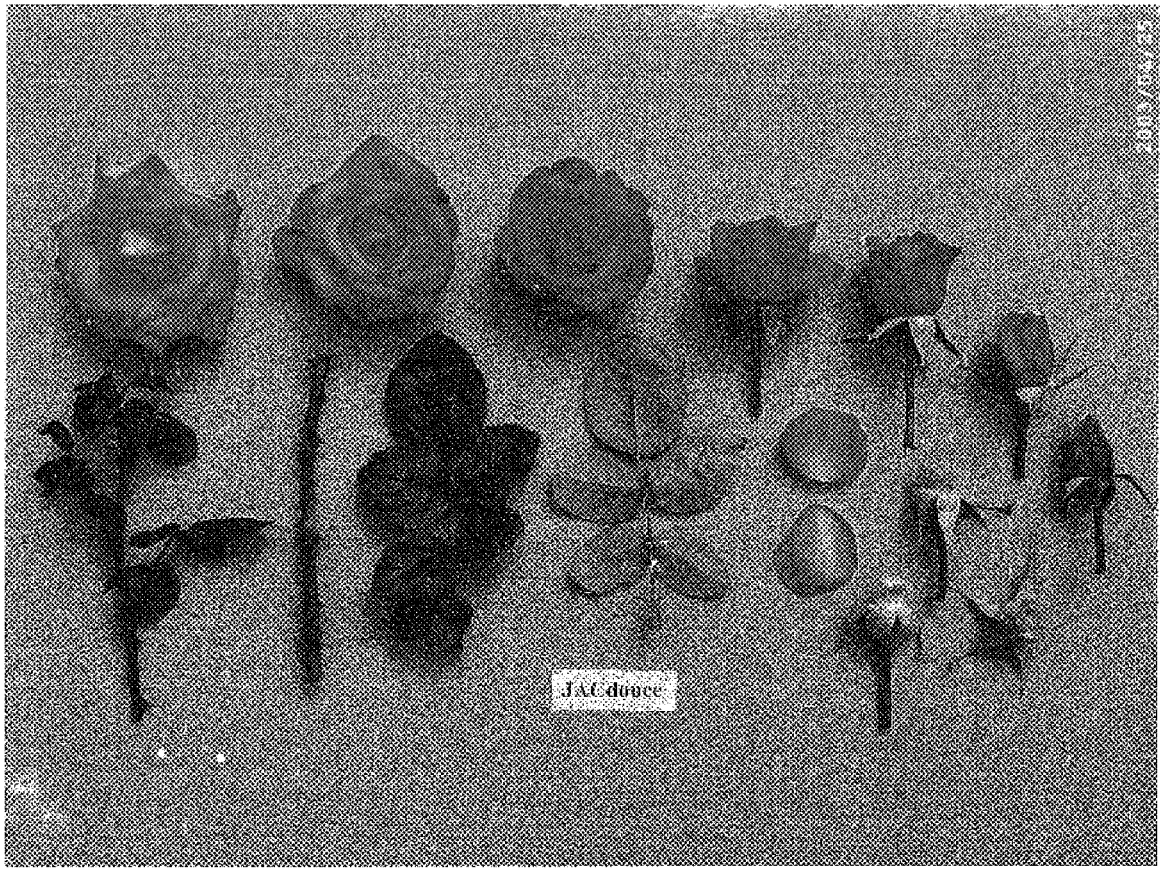
J.A.C douce